United States Patent [19]
Kobrin et al.

[11] Patent Number: 5,936,150
[45] Date of Patent: *Aug. 10, 1999

[54] THIN FILM RESONANT CHEMICAL SENSOR WITH RESONANT ACOUSTIC ISOLATOR

[75] Inventors: Paul H. Kobrin, Newbury Park; Charles W. Seabury, Calabasas; Alan B. Harker, Thousand Oaks, all of Calif.; Ronald P. O'Toole, Cedar Rapids, Iowa

[73] Assignee: Rockwell Science Center, LLC, Thousand Oaks, Calif.

[ * ] Notice: This patent is subject to a terminal disclaimer.

[21] Appl. No.: 09/063,307

[22] Filed: Apr. 13, 1998

[51] Int. Cl.$^6$ .............................. G01N 7/00; H01L 41/04
[52] U.S. Cl. ........................................... 73/24.06; 310/324
[58] Field of Search .......................... 73/24.06; 310/324, 310/311, 321, 338, 313 D, 187

[56] References Cited

U.S. PATENT DOCUMENTS

| | | | |
|---|---|---|---|
| 4,166,967 | 9/1979 | Benes et al. | 310/338 |
| 4,383,194 | 5/1983 | Ohigashi et al. | 310/326 |
| 4,479,070 | 10/1984 | Frische et al. | 310/338 |
| 4,771,205 | 9/1988 | Mequio | 310/334 |
| 5,406,829 | 4/1995 | Ravel et al. | 73/24.01 |
| 5,629,906 | 5/1997 | Sudol et al. | 367/162 |
| 5,646,583 | 7/1997 | Seabury et al. | 333/187 |

OTHER PUBLICATIONS

Grate et al, "Surface Acoustic Wave Vapor Sensors Based on Resonator Devices", *Analytical Chemistry*, vol. 63, No. 17, pp. 1719–1727, Sep. 1, 1991.

Ronald P. O'Toole et al., "Thin Aluminum Nitride Film Resonators: Miniaturized High Sensitivity Mass Sensors", *Analytical Chemistry*, vol. 64, No. 11, Jun. 1, 1992, pp. 1289–1294.

Seabury et al., "Thin Film ZnO Based Bulk Acoustic Mode Filers", *IEEE MTT–S D*, 0–7803–3814, Jun. 1997, pp. 181–184.

Olutade et al., "Sensitivity Analysis of the Performance of a Solidly Mounted Thin Film Bulk Acoustic Resonator Ladder Filter", School of Electrical and Computer Engineering and the Microelectronics Research Center, Georgia Institute of Technology, Dec. 4, 1996, pp. 1–19 plus drawings.

*Primary Examiner*—Hezron Williams
*Assistant Examiner*—Jay L. Politzer
*Attorney, Agent, or Firm*—Koppel & Jacobs

[57] ABSTRACT

A miniature chemical sensor using a thin film acoustic resonator coated with a chemically sensitive sorbent coating. The thin film acoustic resonator has electrodes separated by a thin piezoelectric layer and is supported by a multilayer resonant acoustic isolator. The resonant acoustic isolator has alternating layers of high and low acoustic impedance material, each layer being one quarter acoustic wavelength thick or an odd multiple thereof at the resonant frequency. The resonant acoustic isolator is solidly mounted on a substrate but provides acoustic isolation between the thin film acoustic resonator and the substrate at a resonant frequency.

14 Claims, 2 Drawing Sheets

THIN FILM RESONANT CHEMICAL SENSOR WITH RESONANT ACOUSTIC ISOLATOR

BACKGROUND OF THE INVENTION

1. Field of the Invention

This invention relates to miniature, low-level chemical sensors, and particularly to miniature chemical vapor sensors utilizing thin-film acoustic resonators (TFR's).

2. Description of the Prior Art

There is a need to detect vapors at extremely low levels for numerous purposes. Applications include the detection of buried mines, chemical warfare agents, pollutants, proscribed substances, unexploded munitions, or food spoilage. Ideally a sensor for low level vapor detection should be miniature, durable, temperature stable, and extremely sensitive.

Acoustic transducers coated with chemical sorbates have been used as mass transducers to detect vapors. Various coatings may be used to selectively adsorb the vapor of interest. A small adsorbed mass changes the resonant frequency of the transducer. This change in resonance can then be detected electronically with high precision.

One type of acoustic transducer known as a Thin Film Resonator (TFR) is particularly advantageous for the detection of vapors. TFR's offer advantages because they are smaller and may operate at higher frequencies than other mass transducers, with less degradation from the addition of a sensitizing coating. Small size also offers other advantages such as the ability to lock multiple sensors in close thermal contact, ease of introducing the vapor with uniformity, and ease of production and packaging. Small free standing TFRs have been demonstrated as mass transducers by O'Toole et al, *Analytical Chemistry*, Vol. 64, No. 11 (Jun. 1, 1992).

To achieve high sensitivity in a TFR sensor, it is desirable that the device be extremely thin. This can be shown by considering the equations governing the resonant frequency of a bulk acoustic resonator. The bulk acoustic resonator is fabricated by placing thin conductive electrodes on the opposing faces of a thin piezoelectric layer. The sandwich thus formed resonates when its thickness is equal to a multiple of one half an acoustic wavelength. When material is added to one of the electrode faces—for instance, by adsorption upon a sorbent surface—the resonant path length increases and the acoustic frequency decreases. For small additions of mass, the change in resonant frequency is given by the Sauerbrey equation, $$\Delta f / f_0 = \frac{\Delta m}{\rho d}$$

where $\Delta m$ is the adsorbed mass per unit surface area, $f_0$ is the initial resonant frequency, d is the thickness and $\rho$ the density of the resonator. If we define the mass sensitivity, Sm of the mass transducer for small changes in mass as Sm= $(\Delta f/f_0)(1/\Delta m)$, then the sensitivity is:

$$Sm = -\frac{1}{\rho d}$$

where d is the resonator thickness. Since the sensitivity is inversely related to resonator thickness, a thin film resonator is expected to have an extremely high mass sensitivity. As the frequency of operation is inversely related to the thickness, extremely thin film resonators operate at extremely high frequencies, in the gigahertz regions.

Unfortunately, extremely thin film resonators required for high frequency operation are difficult to fabricate, sensitive to stress, and very fragile. In order to resonate well, with high Q, the acoustic resonator must be acoustically isolated from its mechanical support, much as a gong must be suspended to ring clearly. This isolation prevents dampening and allows free oscillation of the resonator. In the prior art design used by O'Toole, supra, the electrodes and the piezolectric are acoustically isolated as suspended structures, with a portion of the substrate removed beneath the resonator. This leaves the thin resonator suspended much like a membrane. Suspension provides the necessary acoustic isolation, but the resulting structure is unavoidably fragile. The fragility in turn imposes a lower limit on the practical size of such TFR's and a corresponding upper limit on the practical frequency of operation.

Besides being inherently fragile, suspended TFR chemical sensors are difficult to fabricate, handle and package. Also, intrinsic compression stress of the sputtered piezoelectric films produces distortion, and thus poor reproducibility and yield.

SUMMARY OF THE INVENTION

The present invention seeks to provide a miniature chemical sensor using a thin film resonator which is sensitive, durable, easily fabricated, extremely thin, insensitive to stress, and capable of operation at very high frequencies (up to 10 GHZ).

The sensor is also insensitive to variation in temperature and may be operated in a side-by-side or array configuration that reduces errors due to temperature drift, stress, or other factors.

These goals are accomplished by mounting a thin film acoustic resonator solidly upon a multilayer resonant acoustic isolator, which is in turn solidly supported by a substrate. The thin film acoustic resonator is coated with a thin sorbent layer which may be chemically sensitive to the chemical to be sensed.

A key feature of the invention is the multilayer resonant acoustic isolator. This isolator is formed upon a solid substrate and comprises a stack of alternating layers of low and high acoustic impedance materials, each layer having a thickness equal to ¼ the acoustic wavelength (or an odd multiple thereof) at a resonant frequency. This configuration forms the acoustic analog of an (optical) Bragg reflector. Acoustic waves crossing the boundary from a high to a low acoustic impedance layer produce a reflected wave with phase inversion; similarly, acoustic waves crossing a boundary from a low impedance material to a high impedance material will produce a reflection but without phase inversion. Because of the ¼ wave layer thickness, reflected waves from successive underlying boundaries arrive in phase with reflecting waves at overlying boundary surfaces and reinforce constructively. By providing multiple ¼ wave layers of alternating high and low impedance materials, very high acoustic reflectivity may be obtained. At or near the resonant frequency the acoustic isolator thus provides near perfect acoustical isolation, while still providing solid mechanical support to the overlying thin film resonator.

In order to detect a chemical, the chemical of interest (usually a vapor) is brought into contact with and interacts with the exposed sorbent surface coating, causing the mass and/or the mechanical properties of the sorbent coating layer to change. In general this change will be an increase in mass due to adsorption or absorption by the sorbent layer, but the sorbent coating may also be chemically sensitive, so that subtle changes in its mechanical properties may occur. In either case, the changes in the sorbent coating will cause a change in the resonant frequency of the thin film acoustic resonator, as the coating lies directly upon the resonator and is a part of the acoustic resonant path. The change in resonant frequency can then be measured electronically and interpreted. Various configurations, including side-by-side or arrayed sensors, may be employed to achieve temperature compensation or signal enhancement through electronic signal processing.

The use of the ¼ wave stacked, resonant acoustic isolator offers advantages over previous approaches: solid contact with the substrate eliminates stress induced film distortion, giving more consistent results; resonators mounted on the stacked isolator are less fragile than resonators isolated by suspension; because the solid support enables easy fabrication of smaller resonators, large numbers of TFR's may be fabricated on each substrate for low cost production and easy packaging; and multiple resonators thus fabricated may be easily kept in close thermal contact. Smaller size also offers advantages in thermal stability and in reducing the thermal regulation power requirements.

An additional feature in the preferred embodiment of the invention is the use of aluminum nitride (AlN) as a piezoelectric material, and in particular the use of AlN with one or more layers of silicon dioxide ($SiO_2$)added. Careful adjustment of the thickness of $SiO_2$ layer results in a very small temperature coefficient of the resonant frequency, and excellent temperature stability.

DETAILED DESCRIPTION

Figure 1:
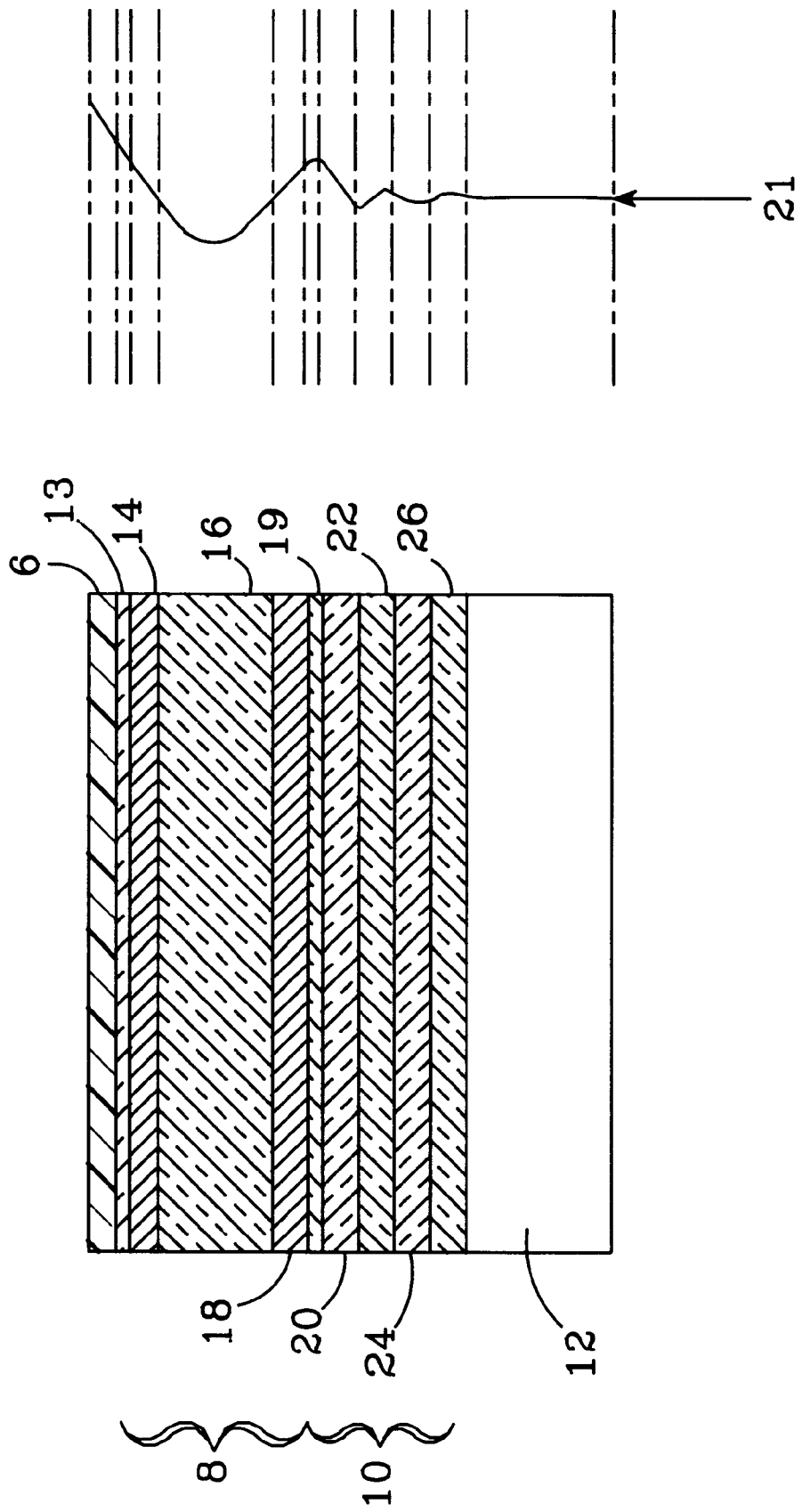
FIG. 1 is a sectional view of a thin film resonant chemical sensor which incorporates the present invention.

FIG. 1 illustrates the invention in lateral cross section. It may usefully be considered as four functional blocks: The sorbent surface coating 6; The thin film acoustic resonator 8; the resonant acoustic isolator 10; and the substrate 12. All four functional blocks are stacked in a laminar manner, surfaces in full contact.

The sorbent surface coating 6 is coated upon the upper exposed area of the thin film acoustic resonator 8, with the upper surface of the coating exposed to the gas containing the chemical to be sensed. When the detectable chemical is brought into contact with the sorbent surface coating 6, the coating may absorb, adsorb, or otherwise undergo chemical or mechanical changes in response to the detectable chemical. A variety of materials may be used for the sorbent coating 6 as discussed below.

The thin film acoustic resonator 8 comprises 3 essential elements: a top electrode 14, piezoelectric layer 16, and bottom electrode 18. Additional layers of $SiO_2$, 13 and 19 may be added for temperature compensation, as explained below. The thickness of the piezoelectric layer primarily determines the resonance frequency of the device. The piezoelectric layer 16 typically has a thickness equal to ½ the effective acoustic wavelength at the resonance frequency, but it is also possible to achieve resonance at harmonics of the fundamental frequency, for which the piezoelectric layer would have a thickness equal to an integer multiple of ½ acoustic wavelength. As the sorbent surface coating 6 is solidly connected to the thin film resonator 8, it forms a part of the acoustic structure. Thus, small changes in the mass or characteristics of the sorbent surface coating 6 will cause a slight shift in the resonant frequency. The shift in resonance frequency provides a signal indicating the presence of a detectable chemical (usually a vapor).

To achieve narrow band, high Q resonance it is critical that the thin film acoustic resonator 8 be acoustically isolated or suspended so that it may resonate freely, without loss of energy to the surrounding materials. The resonant acoustic isolator 10 supports the acoustic resonator 8 mechanically while it isolates it acoustically, allowing it to resonate without significant dampening at the resonant frequency.

Resonant acoustic isolator 10 comprises a stack of alternating layers of low and high acoustic impedance materials, shown as layers 20, 22, 24 and 26. It should be understood that although four such layers are shown, a greater number may be used, and in general from five to nine layers are desirable. It is critical that each such layer have a thickness substantially equal to ¼ the acoustic wavelength in the material at resonance (or an odd integer multiple of ¼ wavelength). This configuration forms the acoustic analog of an (optical) Bragg reflector. Acoustic waves crossing the boundary from a high acoustic impedance layer to a low acoustic impedance layer are partially reflected (with inversion) and partially transmitted. Similarly, acoustic waves crossing a boundary from a low impedance material to a high impedance material are partially reflected (but without inversion). As each of the layers 22 through 26 are ¼ wavelength thick, the returning reflections from the underlying layer boundaries are advanced in phase relative to the reflection at the overlying boundary by the round trip phase of ¼ wave (downward path) plus ¼ wave (return path) for a total of ½ wave (n radians). The reflected wave from an underlying boundary will thus arrive in phase with the (inverted) reflection at the layer boundary overlying at ¼ wavelength above, assuming propagation normal to the layers. The ¼ wavelength layer thickness thus insures that reflected waves from successive underlying boundaries arrive in phase with reflecting waves at overlying boundary surfaces and reinforce constructively. In the multilayer stack of ¼ wave layers all such reflections will tend to reinforce, while the downward transmitted acoustic wave will be attenuated as it continues down through the stack.

By providing multiple ¼ wave layers of alternating high and low impedance material, very high acoustic reflectivity may be obtained from the resonant acoustic isolator 10. This allows nearly all of the acoustic energy to be reflected back into the thin film acoustic resonator 8 instead of being transmitted downward into the substrate where the energy would be absorbed and dissipated. The resonant acoustic isolator 10 thus allows the thin film acoustic resonator 8 to resonate freely without damping from loss of acoustic energy to the substrate 12 or the environment. The resonant acoustic isolator of the present design does not sacrifice solid mechanical support to accomplish acoustic isolation. This is a significant advantage over prior art suspended resonator designs: At or near the resonant frequency the acoustic isolator thus provides near perfect acoustical isolation between the thin film acoustic resonator 8 and the substrate 12 while otherwise providing solid mechanical support.

The confinement of the acoustical mode within the thin film acoustic resonator is also illustrated in FIG. 1. This acoustic strain field 21 is shown as a plot of magnitude of strain on the horizontal scale as a function of depth within the sensor. The strain is at its maximum near center of the thin film acoustic resonator 8, is attenuated passing through layers 20 through 26 of the resonant acoustic isolator, and diminishes to near zero at the substrate. It can be seen that the acoustic energy is effectively confined to the thin film acoustic resonator 8.

The substrate 12 provides support and a base for fabrication and is typically either high resistivity Silicon or $SiO_2$. The substrate may also be glass or gallium arsenide (GaAs). If Silicon (relatively high acoustic impedance) is used then the resonant acoustic isolator 10 should comprise an odd number of layers with a low impedance layer next to the substrate, to preserve the low/high impedance alternating pattern. It is convenient if the substrate is an electrically insulating material so that devices may be electrically isolated for connection.

The present invention lends itself to fabrication by standard techniques. Multiple devices may be fabricated on a single substrate in various configurations by patterning at least the top electrode into a series of mutually separated electrodes for the different sensors. A large area capacitively coupled AC connection to the bottom electrode can be used to avoid the need for connections through the piezoelectric, as shown in FIG. 4.

The sorbent surface layer is frequently an organic polymer and should be chosen to achieve selectivity and sensitivity to the subject chemical of interest. Since organic sorbent coatings tend to be acoustically lossy materials, a significant coating thickness degrades the quality of the acoustic resonance. This places a practical limit on the thickness of the coating. Coatings in the 20 to 100 nm. range are effective.

The sorbent surface coating may be applied by various means. The coating may be sprayed onto the TFR even after it is bonded into a package. Covalently bonded coatings may be applied by placing the package into a reactive solution. Spin coating is possible, or a frozen dilute mixture of a polymer in a solvent may be used as a deposition target for pulsed laser deposition.

Figure 2:
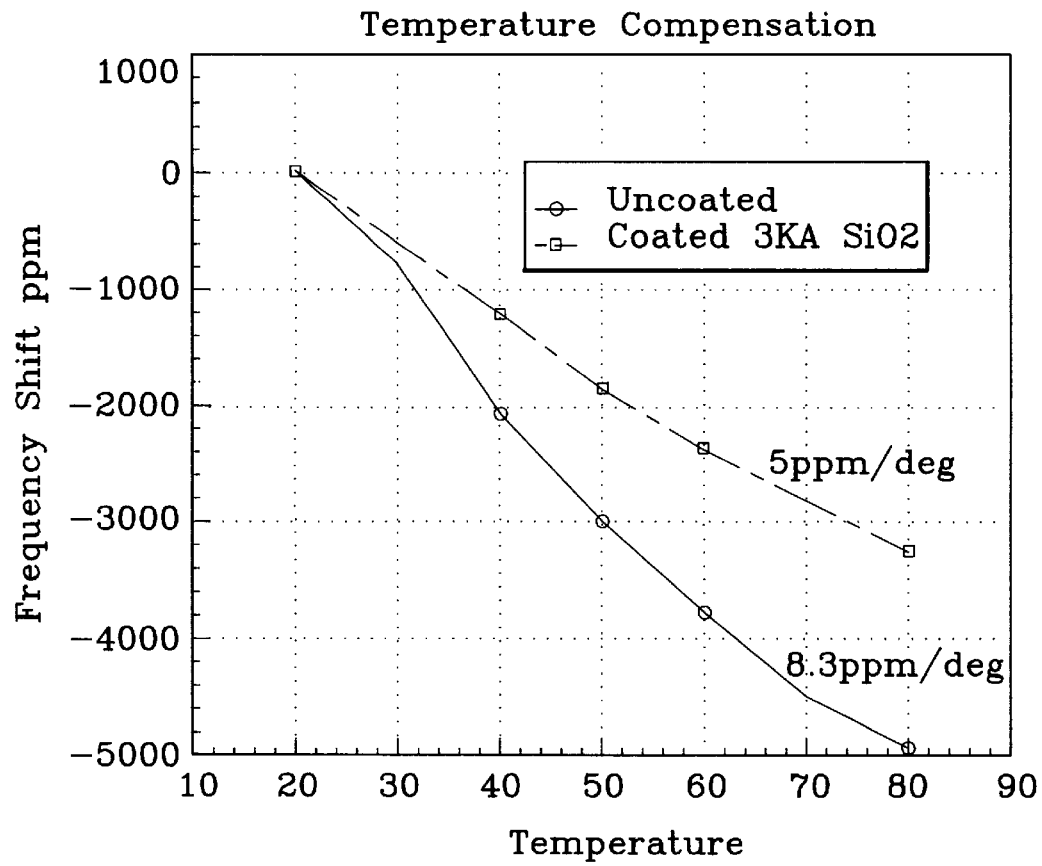
FIG. 2 is a graph illustrating the temperature compensation that can be achieved by the addition of an $SiO_2$ layer to the piezoelectric.

In the preferred embodiment, the piezoelectric layer 16 is fabricated from AlN. AlN is preferred because of its higher quality factor and lower chemical reactivity, although other materials such as ZnO may be used. AlN has a negative temperature coefficient of acoustic velocity (approx. −30 ppm/deg. C) which normally causes the resonant frequency of the TFR to decrease with temperature. To reduce this problem it is possible to add a thin layer of $SiO_2$, which has a positive temperature coefficient of acoustic velocity (approx. +80 ppm/deg. C.) into the acoustic structure. By carefully adjusting the $SiO_2$ content one can achieve a very low device temperature coefficient. FIG. 2 plots the temperature vs. frequency shift characteristics of a typical $SiO_2$ compensated device. The Figure shows the effect of adding a 3000 Angstrom $SiO_2$ thickness in two layers to a resonator with approximately 1.5 micron total thickness. The two added $SiO_2$ layers 13 and 19 are shown in FIG. 1.

In fabricating the resonant acoustic isolator, Hafnium Oxide ($HfO_2$) is preferred as the high acoustic impedance material in the high impedance layers 22 and 26 (and alternating layers if more are to be added). It can be deposited by sputtering or electron beam bombardment evaporation with concurrent ion bombardment to form a hard, dense dielectric having a relatively high acoustic impedance (approximately 40 $Kg/m^2s$). Silicon Dioxide ($SiO_2$) is preferred for the low impedance material because it is ubiquitous in the semiconductor industry, because it has a very low intrinsic acoustic loss with relatively low acoustic impedance (Z of approximately 13 $Kg/m^2s$), and because it can be deposited using a variety of convenient methods, such as thermal evaporation, ion assisted thermal evaporation, or electron beam evaporation.

Hafnium Oxide films evaporated at low temperatures have been found to be acoustically lossy. Raising the substrate temperature above 400 degrees C. during fabrication increases the density, but the films become polycrystalline with rough surfaces that produce unacceptable acoustic scattering. However, electron beam evaporation with concurrent ion bombardment is known in the prior art to achieve the required bulk density and hardness while maintaining a smooth surface. Such films exhibit low acoustic loss. Very high reflectivity layers have been produced by this method, resulting in high performance from the acoustic isolator.

Figure 3:
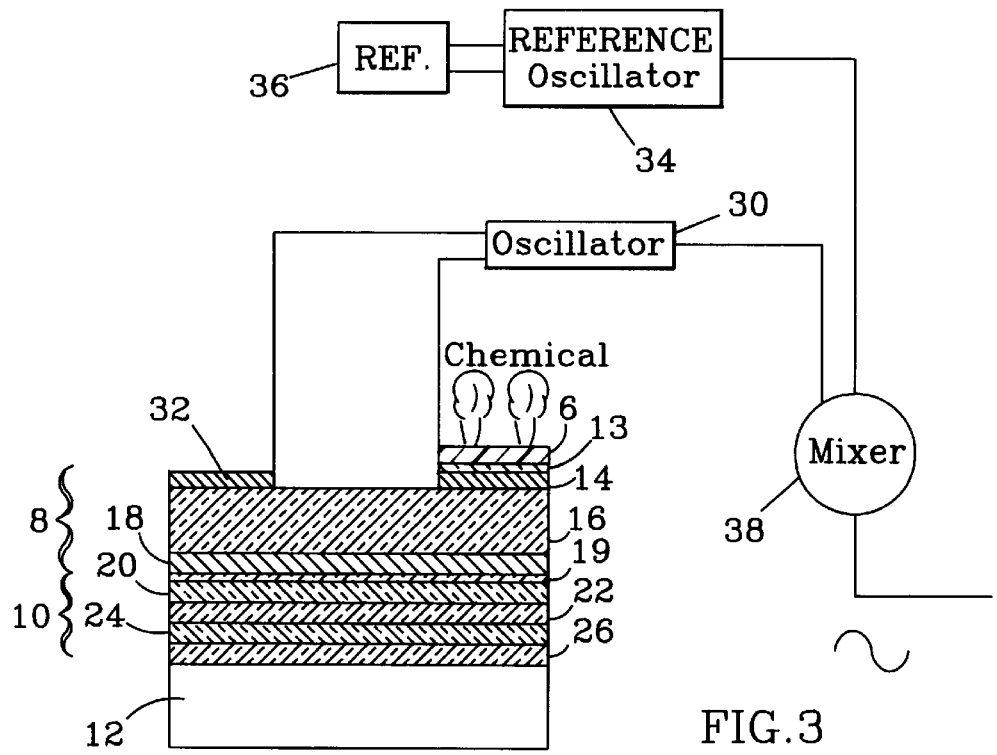
FIG. 3 is a block diagram showing how the invention may be used.

One way of using the invention is shown in FIG. 3. Sensor 29 is brought into contact with the chemical to be sensed. The electrodes of sensor 29 are connected as the frequency reference in the feedback loop of an oscillator circuit. Electrode 32 is capacitively coupled to electrode 18, providing AC signal coupling through the piezoelectric layer 16. Electrode 14 is connected to the frequency reference terminal of oscillator 30. A frequency reference oscillator 34 is controlled by an independent frequency reference 36, which may be another sensor in a different chemical environment or may be another other type of frequency reference. The output signals of oscillator 30 and frequency reference oscillator 34 are mixed by mixer 38, producing an output at a frequency equal to the difference between the sensor signal and the reference signal. The frequency of the output of mixer 38 indicates the presence of the chemical of interest and may be measured electronically. Other methods of measuring the shift in resonance frequency are possible, such as driving the sensor actively and measuring the impedance.

Excellent temperature stability may be obtained if the sensor is maintained in a temperature controlled environment such as a thermostatic oven and the gas collected and brought to the sensor.

The firmly supported device of the present invention offers significant advantages over prior suspended thin film resonant sensors. Because of the resonant acoustic isolator, the new chemical sensor is more solidly supported by the substrate, eliminating stress induced film distortion, giving more consistent results and offering the potential for low cost through conventional batch processing and simpler packaging. It is more durable, more easily fabricated, and more compact. Because the thin film resonator may be made very thin, it is more extremely sensitive, and capable of very high frequency operation (up to 10 GHz). The invention may be made insensitive to temperature variation and may be further compensated by comparison with a frequency reference, as described above.

While particular embodiments of the invention have been shown and described, numerous variations and alternate embodiments will occur to those skilled in the art. Accordingly, it is intended that the invention be limited only in terms of the appended claims.

We claim:

1. A chemical sensor for sensing chemicals in an environment, comprising:

a substrate;

a chemically sensitive thin-film acoustic resonator, comprising:

a piezoelectric resonator having an acoustic resonance quality, and an organic coating on a surface of said piezoelectric resonator and exposed to the environment, said coating and said piezoelectric resonator together having an acoustic resonance quality less than that of said piezoelectric resonator by itself; and a resonant acoustic isolator, interfacing between said chemically sensitive thin film acoustic resonator and said substrate and having a resonant frequency substantially matching that of said thin film acoustic resonator, thereby acoustically isolating said chemically sensitive thin film acoustic resonator from said substrate at said resonant frequency.

2. The chemical sensor of claim 1, wherein said resonant acoustic isolator comprises alternating low acoustic impedance layers and high acoustic impedance layers, and wherein said piezoelectric resonator has a thin piezoelectric film with a thickness substantially equal to an integer multiple of a half wavelength of a bulk acoustic wave propagating normal to the surface of said film at said resonant frequency.

3. The chemical sensor of claim 2, wherein said integer multiple of a half wavelength equals one-half wavelength, and wherein said resonant frequency is in the range of 1–10 Gigahertz.

4. The chemical sensor of claim 3, wherein each of said low acoustic impedance layers and high acoustic impedance layers has a thickness substantially equal to an odd integer multiple of one-quarter acoustic wavelength at the resonant frequency of said thin film acoustic resonator.

5. The chemical sensor of claim 4, wherein said coating has a thickness in the range of 20 to 100 nanometers.

6. The chemical sensor of claim 3, further comprising a temperature compensating material on said electrodes with positive temperature coefficient of acoustic velocity that compensates for a a negative temperature coefficient of acoustic velocity of said piezoelectric material.

7. The chemical sensor of claim 6, wherein said compensating material comprises silicon dioxide ($SiO_2$).

8. The chemical sensor of claim 7, wherein said high acoustic impedance layers comprise hafnium oxide ($HfO_2$).

9. A chemical sensor array for sensing chemicals in an environment, comprising:

a common substrate;

a plurality of chemical sensors, fabricated on said common substrate, each chemical sensor comprising:

a chemically sensitive thin-film acoustic resonator, comprising:

(a) a piezoelectric resonator having an acoustic resonance quality, and (b) an organic coating on a surface of said piezoelectric resonator and exposed to the environment, said coating and said piezoelectric resonator together having an acoustic resonance quality less than that of said piezoelectric resonator by itself, and a resonant acoustic isolator, interfacing between said chemically sensitive thin film acoustic resonator and said common substrate and having a resonant frequency substantially matching that of said thin film acoustic resonator, said acoustic isolator acoustically isolating said chemically sensitive thin film acoustic resonator from said common substrate at said resonant frequency.

10. The sensor array of claim 9, wherein said resonant acoustic isolators comprise alternating low acoustic impedance layers and high acoustic impedance layers, and wherein said piezoelectric layer has a thickness substantially equal to an integer multiple of a half wavelength for a bulk acoustic wave propagating normal to the surface of said resonator's thin film at said resonant frequency.

11. The sensor array of claim 10, wherein said resonant frequency is in the 1–10 Gigahertz range.

12. The sensor array of claim 11, wherein said sensors share a common resonant acoustic isolator.

13. The sensor array of claim 12, wherein said sensors share a common bottom electrode.

14. The sensor array of claim 13, wherein said sensors share a common piezoelectric layer.

* * * * *